United States Patent
Toda (10) Patent No.: US 6,755,799 B2
(45) Date of Patent: Jun. 29, 2004

(54) BELT-LIKE CORSET

(76) Inventor: Yoshitaka Toda, 9-2 Esaka-cho 5-chome, Suita, Osaka (JP), 564-0063

( * ) Notice: Subject to any disclaimer, the term of this patent is extended or adjusted under 35 U.S.C. 154(b) by 0 days.

(21) Appl. No.: 10/227,009

(22) Filed: Aug. 22, 2002

(65) Prior Publication Data

US 2003/0050584 A1 Mar. 13, 2003

(51) Int. Cl.$^7$ .............................. A61F 5/00; A41F 9/00
(52) U.S. Cl. ............................... 602/19; 2/311
(58) Field of Search ............................ 602/19, 60, 61; 128/876, 96.1, 100.1, 102.1; 2/311, 312, 338, 44; 450/155

(56) References Cited

U.S. PATENT DOCUMENTS

| | | | | |
|---|---|---|---|---|
| 1,184,581 A | * | 5/1916 | Sigurini ..................... 450/121 |
| 1,940,904 A | * | 12/1933 | Dayton et al. ............... 602/19 |
| 3,536,357 A | * | 10/1970 | Murcott ..................... 297/485 |
| 5,257,419 A | * | 11/1993 | Alexander ..................... 2/44 |
| 5,363,863 A | * | 11/1994 | Lelli et al. ................. 128/876 |
| 5,388,274 A | * | 2/1995 | Glover et al. .................. 2/338 |
| 5,548,843 A | * | 8/1996 | Chase et al. ................... 2/102 |
| 5,551,085 A | * | 9/1996 | Leighton ......................... 2/44 |
| 5,586,969 A | * | 12/1996 | Yewer, Jr. ..................... 602/19 |
| 5,634,891 A | * | 6/1997 | Beczak et al. ................ 602/19 |
| 5,690,609 A | * | 11/1997 | Heinze, III .................. 602/19 |
| 5,728,056 A | * | 3/1998 | Seriguchi et al. ............. 602/19 |
| 6,099,490 A | * | 8/2000 | Turtzo ......................... 602/19 |
| 6,102,879 A | * | 8/2000 | Christensen et al. .......... 602/19 |

\* cited by examiner

*Primary Examiner*—Nicholas D. Lucchesi
*Assistant Examiner*—Huong Q. Pham (57) ABSTRACT

This present invention relates to a novel belt-like extension corset providing for anterior to posterior traction from the sides to the back at waist level comprising two longitudinally expandable front and back belt members each having an inner and outer surface, means to attach said belt members at their longitudinal centers, means for attaching the longitudinal ends of the front belt member, two direction changing means for said back belt member located on the outer surface of the front belt member positioned so as to be present on the left and right side when worn, and means for attaching the longitudinal ends of the back belt member to the outer surface of the back belt member lateral to its middle portion. The corset can shorten a number of days of treatment, for example, a number of days required for treatment of muscular low back pain.

6 Claims, 7 Drawing Sheets

The Conventional Corset Fixed Specifically At The Abdomen

FIG. 10

The Corset Of The Invention
Fixed Anteriorly And Posteriorly

FIG. 11

Forward Bending Angle Of Conventional Type Corset Group

FIG. 12

Forward Bending Angle Of Corset Group Of The Invention

BELT-LIKE CORSET

PRIORITY CLAIMED

This application claims priority based on Japanese application number 2001-253516, filed Aug. 23, 2001.

FIELD OF THE INVENTION

The present invention relates to a belt-like corset for use in the treatment of low back pain (hereinafter "LBP").

BACKGROUND OF INVENTION

Low back pain affects more than 60% of the United States adult population at some time during their lives. Each year in the United States billions of dollars are lost in wages and direct medical costs for low back pain. Consequently, lumbar back belts have gained popularity in many industries under the assumption that their use will reduce low back injuries and thereby decrease medical costs. Majkowski G R et al, 23(19) SPINE 2104–9, 2104 (1998)

Conservatively, low back pain is treated with joint manipulation, myofascial therapy, a combination of both, or "back school." Back school is a program that teaches patients the recommended sitting and standing neutral postures, body mechanics, and exercises. In a randomized, assessor-blinded clinical trial of 206 patients, the only significant difference between these treatments after three weeks was a higher pain score with myofascial therapy alone compared with combined therapy. Back school was shown to be as effective as the other procedures. Hsieh, C j et al, 27(11) SPINE 1142–8 (2002).

Low back pain may be associated with disc herniation, disc degeneration and segmental instability and has been treated with gravitational traction by suspending the patient in a hanging, upright position to widen the intervertebral space. It is associated with increased lordosis that is measured by Ferguson's angle, the angle between the base of the sacrum and the horizontal. Harrison D D et al, 11(5) J Spinal Disorders 430–439, 434 (1998). In a study on the effect of suspension traction, both patients and controls showed a significant increase in Ferguson's angle during traction and an increase in the distance between L1 and S1. Tekeoglue I, et al 23(9) SPINE 1061–1064 (1998).

Exactly why people with low back pain benefit from wearing a lumbar corset remains unclear, but restriction of motion, decreased disc pressure and changes in posture are most often cited, Thoumie P, et al, 13(1) CLIN BIOMECH 18–26, 19 (1998). One concept of back supports is to increase intra-abdominal pressure to produce a rigid tube effect that promotes decompression and posterior vectors, both of which should aid in the decompression of the spine and decrease the load on the extensors. Ciriello V M & Snook, S H J, 20(11) SPINE 1271–1278 (1995). Other groups report that the corset is of no benefit and should never be prescribed unless a patient has already used it successfully. Helliwell P S & Wright V, 30(1) BR J RHEUMATOL 62 (1991). When the Freeman Lumbosacral Corset was compared with the conservative treatments of spinal manipulation, transcutaneous muscle stimulation and massage in patients with subacute low back pain, no significant differences were observed. Pope M H, et al, 19(22) SPINE 2571–7, 2576 (1994).

A conventional corset is comprised of a belt that is stretchable in its longitudinal direction and is applied to the waist portion and wrapped around the body in a state of resisting the contractile force produced when the corset is expanded and specifically, at the abdomen. The the longitudinal ends of the expansion belt member are attached to each other by attachable and detachable means of a face fastener or the like. Thereby, the body is strongly fastened to achieve prevention, alleviation or treatment of low back pain.

Various improvements have been offered. U.S. Pat. No. 4,559,933, to Batard, teaches an orthopaedic lumbo-sacral corset of a plastic material shell which is adaptable to a widened range of corpulencies and is connected along its adjacent dorsal edges by a semi-rigid thin band forming a hinge adapted to be generally aligned with the spine of the wearer so as more clearly to orient the shells, with attachment and tightening structure between the adjacent front edges of the two half-shells and an inflatable lumbar pad forming two symmetrical pads relative to the axis. U.S. Pat. No. 5,634,891, to Beczak teaches a complex arrangement to be wrapped around the torso of a human body and cause an increase in intra-abdominal pressure and a relief in pain associated with disorders of the spinal column. It is comprised of back and front panels held together by expandable straps. U.S. Pat. No. 4,622,957, to Curlee, teaches a therapeutic corset appliance which consists of an elongated rigid or semi-rigid support surface and a flexible bladder disposed on the support surface possessing a low coefficient of stretchability.

The need to restore and maintain the lumbar lordosis has been recognized at least since Hippocrates, at about 400 BC, recommended pressing sharply on the kyphosis of a patient with lumbar pain. McKenzi R A, 89 NZ MED J 22–23 (1979). Prolonged sitting, as in an office, is generally accepted as a high risk factor for low back pain and may decrease lordosis of the lumbar spine. Lengsfeld M, et al, 22 MED ENG PHYSICS 665–9 (2000). The postural benefit of sitting with a lumbar support pillow documents the need to correct lordosis in patients with LBP. Majeske C and Buchanan C, 64 (10) PHYS THER 1531–5 (1984). In contrast, Williams advocated conservative treatment for low back pain based on reducing the lumbosacral angle and recommended that the spine be maintained in flexion when changing position. Williams P C, 5 CLIN ORTHOP 28–40 (1955).

Lumbar lordosis is strongly correlated with sacral inclination in both controls and patients with low back pain (LBP) and was greater in controls, particularly in the sixth decade of life (p<0.001). Increased thoracic kyphosis was seen more in LBP than in controls and the difference was significant after the sixth decade. (p<0.01). The importance of intraoperative positioning for maintenance of physiological lumbar lordosis in patients undergoing instrumented lumbar fusions has been the subject of clinical research. Korovessis P, Stamatakis M, & Baikousis A, 12(2) JL SPINAL DISORD 131–137 (1999). The maximal difference between the lowermost and highest values of lumbar lordosis was significantly greater in the controls (p<0.001). In the controls, the distal (L4–L5) lordosis increased considerably with increasing age. LBP patients, however, showed only a slight increase in the distal lumbar lordosis with age. Based on these observations, chronic LBP patients appear to lose their ability to compensate for the increased thoracic kyphois, and have a more relative hypolordotic lumbar spine than controls. Korovessis, Id. However, other authors have reported that there are no statistically significant differences between patients with acute or chronic pain and normals in thoracic kyphosis or lumbar lordosis. Tuzin et al, 18 CLIN RHEUMATOL 308–312, 311 (1990).

Lumbosacral back belts for back support have been marketed as a significant aid in the prevention of low back pain. Lumbosacral belts have been used in weight lifting by athletes and have been demonstrated to restrict standing flexion, Lantz, S A and Schultz A B 11(8) Spine 834–7, 835 (1996), and improve abdominal muscle strength and lifting capacity in healthy women. Smith E B et al, 21(3) SPINE 356–366 (1996). Researchers have indirectly calculated compressive forces to the spine and concluded that lumbar supports decreased forces affecting the spine. Smith, Id., at 357. Sixty-nine (69) healthy women aged 20 to 40 were studied in a cross-over design, each subject lifting with and without a lumbosacral belt. Of these, 36 were capable of lifting more weight with the belt, 5 lifted less, and there was no change in 28 of the subjects (p<0.0001). At 362–3. Other groups, however, found no significant differences in maximum isokinetic endurance and electromyographic spectral parameters of the back muscles as a result of wearing a back belt during heavy lifting and lowering. Ciriello V M & Snook, S H J, 20(11) SPINE 1271–1278 (1995). Finish researchers performed a questionnaire based study of 113 patients using lumbar corsets and found that an elastic corset offered the best help for men and a semirigid high braced corset proved better for women. Alaranta H & Hurri H, 20 SCAND J REHAB MED 133–6, 135 (1988).

To test the efficacy of a lumbar corset into which a spinal support made of heat-mouldable plastic was inserted, 19 patients were randomly assigned to wear a corset manufactured by Johnson and Johnson Ltd with or without the plastic insert in the back pocket. By subjective index, the improvement with the support was significantly greater than in those without the support at 4 and 8 weeks. However, objective measurements by goniometer showed no differences in the changes between the two groups. Researchers postulated that the firm lumbar support may restrict motion and prevent the patient from undertaking movements that precipitate pain. Million R, et al, 40 ANN RHEUM DIS 449–454 (1981).

In studies of the effect of a traditional lumbar belt on radiological and goniometric measurements of lumbar and maximal flexion angles, the lumbar belt decreased lumbar lordosis measured in the orthostatic position to 31 degrees (SD, 10 degrees) from 34 (SD, 11 degrees). These changes were related to the subjects' initial values and the greatest decreases occurred in subjects with the largest initial lumbar curves (R=0.72, p<0.01). In continuous recording tests the changes were similar to those in the single tests. Maximal lordosis angle decreased significantly to 30 degrees (SD, 10 degrees) from 36 degrees (SD, 10 degrees), and mean lordosis angle decreased significantly from 21 degrees (SD 11) to 17 degrees (SD 9) but the decrease in maximal flexion angle was not significant. Thoumi P, supra, at 21.

Scientific literature includes conflicting reports and more work is needed in this area. None of the previously known corsets provides for a contractile anterior to posterior contractile force exerted from the sides of body to the back at waist level.

SUMMARY OF THE INVENTION

There is a need for a lumbosacral corset that will maintain and increase lumbar lordosis. The inventor, an orthopaedic surgeon, intensely studied the possibility of developing a corset capable of shortening a number of days of treatment. This inventor found that the treatment effect was accelerated when lumbar lordosis was maintained and increased by applying anterior to posterior traction force from the sides of the body to the back at the waist.

One object of this invention is to provide a means to create a contractile anterior to posterior force, specifically a belt-like extensile corset comprising two longitudinally expandable front and back belt members each having an inner and outer surface; means to attach said belt members to each other at their longitudinal centers; means for attaching the longitudinal ends of the front belt member; two direction changing means for said back belt member located on the outer surface of the front belt member positioned so as to be present on the left and right sides when worn; and means for attaching the longitudinal ends of the back belt member to the posterior outer surface of the back belt member lateral to its longitudinal center.

Another object of the invention is to provide a corset capable of shortening the number of days of treatment. The corset is convenient for a patient since health insurance is applied to it in a hospital and there has been a desire to develop a corset having a superior treatment effect, that is, capable of shortening the number of days of treatment.

Methods for treating lower back pain are also provided. In a preferred embodiment of the invention, lower back pain in subacute. In another preferred embodiment, it is muscular low back pain. In a most preferred embodiment, the patient is a woman without central obesity.

DETAILED DESCRIPTION OF THE INVENTION

This inventor has discovered that an extensile corset with contractile anterior to posterior traction and a tighter fit pulls the lumbosacral spine into lordosis while the conventional corset decreased sacral inclination in the seated position. Although the mechanism has not been fully elucidated, the reduction may be secondary to abdominal compression by the belt affixed anteriorly with tension from back to front. In patients without central obesity, the conventional corset did not offer the same mechanical protection. Thus, the anatomic effect of the extensile corset, in contrast to the effect of the conventional corset, is more effective for patients without central obesity.

The preferred embodiment of the invention is belt-like corset comprising two longitudinally expandable front and back belt members each having an inner and outer surface; means to attach said belt members at their middle portions; means for attaching the longitudinal ends of the front belt member; two direction changing means for said back belt member located on the outer surface of the front belt member positioned so as to be present on the left and right sides when worn; and means for attaching the longitudinal ends of the back belt member to the outer surface of the back belt member lateral to its longitudinal center.

In a preferred embodiment of the invention, the direction changing means is a ring-like article having two end portions that are attached to opposite lateral edge portions of the front belt member so as extend vertically when the belt is worn by a human.

The belt-like corset may optionally comprise two rigid or semi-rigid strips inserted lattitudinally across front belt member so as to be vertical when the corset is worn.

The front and back belt members may be made of materials well known to those of ordinary skill in the art such as elastic. The opposing ends of the belt members may be secured by means well known to those of ordinary skill in the art such as hooks and eyes, Velcro, buttons, or snaps.

The reason for the improved treatment effect of the corset of the invention is considered to result from the increased inner pressure of the peritoneal cavity by pressing the abdomen, and in addition thereto, the abdominal musculature is reinforced to intensify support force of the bone with regard to the body.

In the conventional belt-like corset, the longitudinal center portion is applied to the waist portion and is attached anteriorly at the abdomen so as to resist the contraction force produced when the corset is expanded. Therefore, a pulling force is exerted in a direction from the posterior waist to the anterior abdomen via that sides. One postulated mechanism is an increase in intra-abdominal pressure. Increases in intra-abdominal pressure produce a rigid tube effect, which may serve to decrease the load on the lumbar paraspinal musculature. Harman E A, Rosenstein R M, Frykman P N, et al, 21 MED SCI SPORTS EXERCISE 186–90 (1989). However, electromyographic analysis in 24 healthy subjects suggested that there is no effect on lumbar paraspinal muscle fatigue or isometric lifting force production as a result of lumbosacral corset use. Majkowski G R, Jovag B W, Taylor B T, et al. 23 SPINE 2104–9 (1998). Other reports also reveal that lumbosacral corsets are not effective for increasing the lifting capacity and strength of paraspinal muscles. Ciriello, supra, Smith E B, Rasmussen A A, Lechner D E, et al, 21 SPINE 356–66 (1996).

An elevated waist-hip ratio may be a risk factor for chronic muscular low back pain in women aged 45 to 69 years with a negative straight leg raise test. Toda Y, Segal N, Toda T, et al, 160 ARCH INTERN MED 3265–9 (2000). Han et al also showed that a high waist-hip ratio was significantly associated with chronic low back pain in women. Han T S, Schouten J S A G, Lean M E J, et al, 21 INT J OBES 21:600–7 (1997). Waist-hip ratio (W/H) is one of the most commonly used anthropometric measures to indicate a central obesity pattern.

Although corsets are worn around the waist, in almost all studies describing the ineffectiveness of lumbosacral corsets, healthy subjects were evaluated without consideration of W/H ratio. It seems reasonable that there may be a difference in the intra-abdominal pressure and subsequent rigid tube effect depending on the degree of central obesity. Thus, particularly in patients with chronic low back pain, it would be helpful to evaluate the relationship between W/H and corset mechanism in order to appropriately select patients for therapy with lumbosacral corsets.

Korovessis et al, supra, reported that lumbar lordosis strongly correlates with sacral inclination in both controls and low back pain patients. Tzün C, et al. 18 CLIN RHEUMATOL 18:308–12 (1999), postulated that both the lumbar lordosis and sacral inclination were increased with body mass index in both healthy subjects and patients with low back pain. It therefore follows that sacral inclination may relate to obesity. While body mass index is commonly used as a measure of obesity, it is not indicative of central obesity, which W/H ratio is a better measure to use in assessing the correlation between central obesity and sacral inclination.

Sacral inclination is also measured by Ferguson's Angle, the lumbosacral angle and the sacral base angle. The sacral base angle is formed when an oblique line is drawn through and parallel to the sacral base and joined with a line drawn horizontally. Harrison, D D et al, supra, at 434, FIG. 3. A sedentary lifestyle due to automobile use and office automation has become widespread in developed societies. Prolonged sitting, especially with poor posture, is known to be a risk factor in low back pain. Majeske, supra. It is well accepted that lordotic posture should be maintained during sitting, and prolonged sitting with a stooped posture is generally accepted as a risk factor for low back pain. Kelsey J L, White III A A, 5 SPINE 133–42 (1980). Thus, this invention is directed at a method to maintain lordosis, preferably in a woman, and most preferably in a woman without central obesity.

A traditional lumbosacral corset consists of a wide wrap-around body belt affixed anteriorly with tension from back to front. Thus, it is plausible that, such a corset may prevent lumbar extension and thereby decrease the lumbar lordosis and sacral inclination. Thoumie et al., supra, demonstrated a significant decrease in the lumbar lordosis of subjects wearing a traditional lumbosacral corset.

This inventor has discovered that if corset tension is reversed, with tension from front to back, it may be possible to increase lumbar lordosis and sacral inclination rather than decreasing it. This in turn relieves low back pain symptoms while sitting. According to the second aspect of the corset, when the direction changing means is formed by the ring-like article, folding back operation is facilitated by inserting the respective two left and right pieces of the back belt member to inner sides of the ring-like articles, which is preferable.

The invention, provides a corset capable of shortening the number of days of treatment, for example, a number of days required for treatment muscular low back pain.

Figure 1:
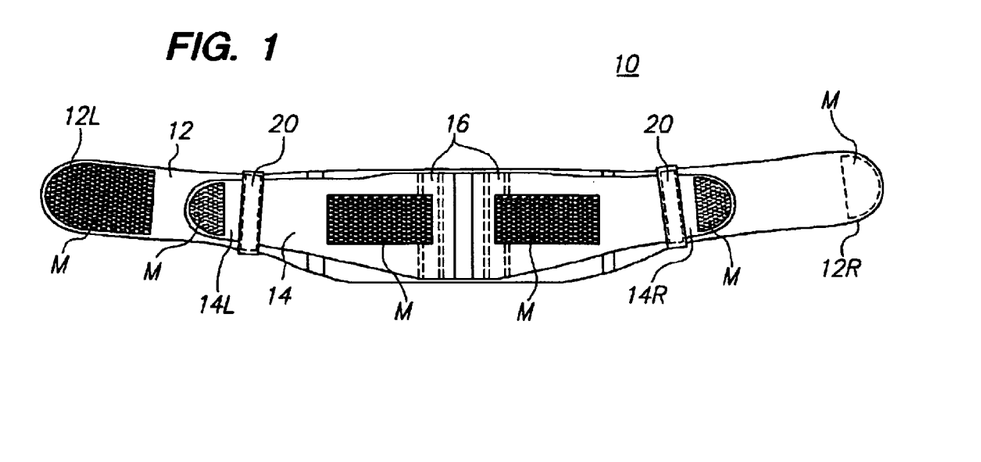
FIG. 1 is a posterior view of a corset according to a preferred embodiment of the invention.
Figure 2:
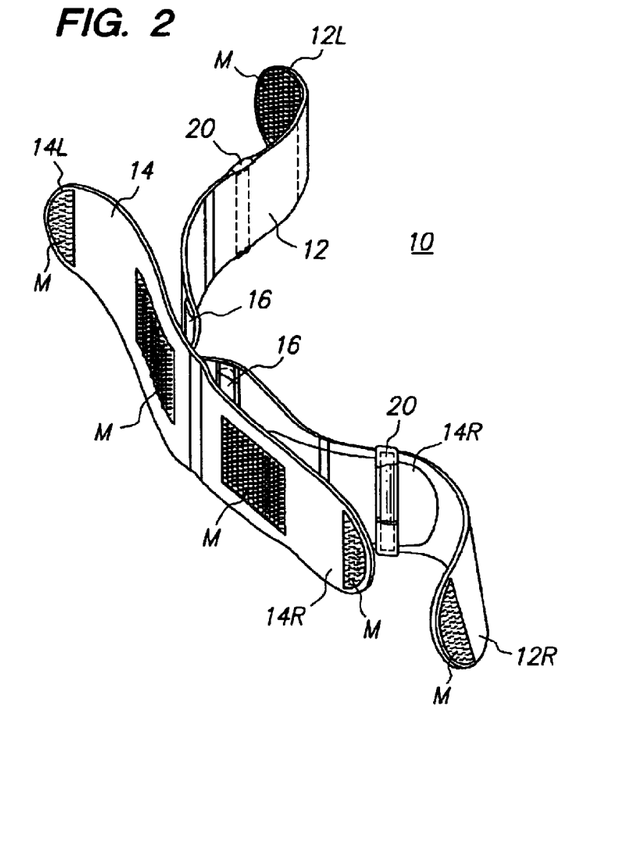
FIG. 2 is a perspective view of FIG. 1.

The invention will be further illustrated by the following non-limiting examples:

FIG. 1 depicts a most preferred embodiment of the corset. FIG. 1 is a posterior view of the corset (10) according to that embodiment of the invention and FIG. 2 is perspective view of the same. In this example, the belts are about 15 cm wide but may range from about 8 centimeters to about 25 centimeters wide, depending on height of the patient. The longitudinal center of the posterior surface of the front belt member (12) expandable longitudinally, is overlapped with the longitudinal center of the anterior surface of the back belt member of the same width (14) and the two centers are attached by means known to those of ordinary skill in the art, such as a seam. The front and back belt members may be made of materials well known to those of ordinary skill in the art such as elastic or any expandable or stretchable material.

If rigid or semi-rigid strips (16) are inserted, the two centers are seamed to maintain a predetermined interval between the centers and the two rigid or semi-rigid strips (16) inserted across the width so as to extend vertically when the corset is worn.

The longitudinal left end (12L) of the front belt member (12), contains a means for attachment (M) on its posterior surface and the longitudinal right end (12R) contains a means for attachment (M) on its anterior surface paired with the above-described face fastener (M) capable of being brought into contact with each other attachably and detachably. The opposing ends of the belt members may be secured by means well known to those of ordinary skill in the art such as hooks and eyes, Velcro, buttons, or snaps.

The lattitudinal center of the posterior surface of the back belt member (14) contains four means for attachment (M) at two locations at predetermined intervals between and at the left and right longitudinal ends (14L, 14R). These may similarly be hooks and eyes, Velcro, buttons, or snaps. There may be a locking means such as a hook made of a metal or made of synthetic resin in place of the Velcro of this example (M).

The direction changing means (20) for the back belt member (14) is attached to the posterior surface of the front belt member between the longitudinal center and ends such that the back belt member may be inserted and folded over it. A total of two of the direction changing means (20) are provided on the left and on the right.

Preferably, the direction changing means (20) are found at about an equidistant position between the longitudinal center and ends, left (12L) and right (12R) of the front belt member (12). The direction changing means (20) is constituted by sealing a core member made of a metal, plastic or made of wood having a diameter of about 5 mm in a slender cloth bag having a length of about 5 to about 7 centimeters, an upper end portion thereof is fixedly attached (seamed) to an upper edge portion of the front belt member (12) and a lower end portion thereof is fixedly attached (seamed) to a lower edge portion of the front belt member (12) to thereby form a ring-like shape. Although the core member may be metal, but is not necessarily metal, it is preferable so that the core member (20) does not extend to a rear side by the pulling force of the folded back belt member (14).

A method of using the corset (10) described above is explained as follows.

Figure 3:
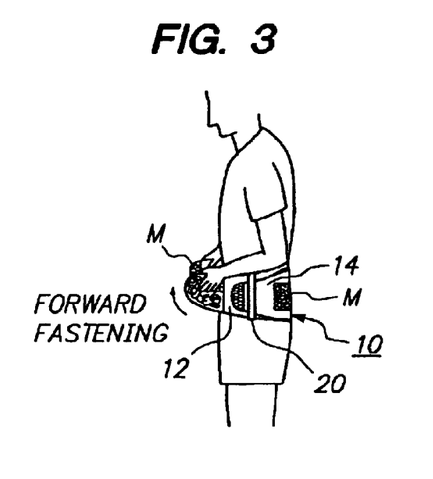
FIG. 3 is an explanatory view showing a subject installing the extensile corset onto his waist and fixing a front belt.
Figure 4:
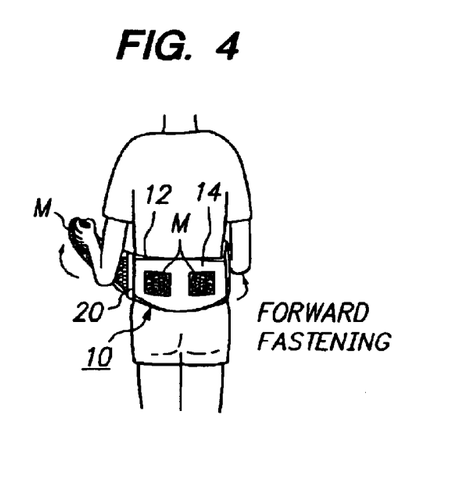
FIG. 4 is a rear view of FIG. 3.

As shown in FIGS. 3 and 4, a subject is installing the anterior surface of the longitudinal center or the corset (10) to the waist portion, the two left and right longitudinal ends (12L, 12R) of the front belt member (12) are held by the hands and wrapped around the body against the contractile force produced when the corset (10) is expanded and at the abdomen, the end portions of the two left and right longitudinal ends (12L, 12R) of the front belt member (12) are attached to each other by the attachable and detachable means of the face fasteners (M) or the like.

Figure 5:
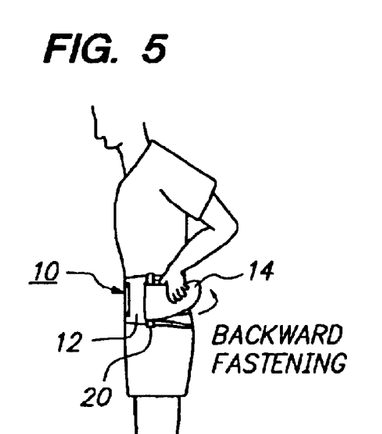
FIG. 5 is an explanatory view showing a subject installing the extensile corset onto his waist and fixing the back belt after fixing the front belt.
Figure 6:
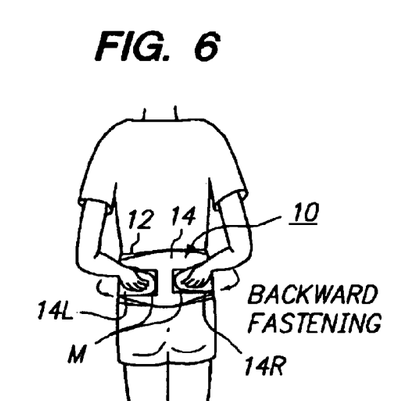
FIG. 6 is a rear view of FIG. 5.
Figure 7:
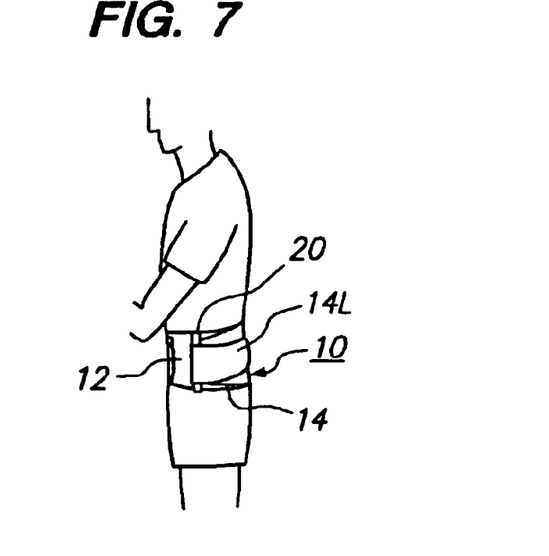
FIG. 7 is an explanatory view of the extensile corset completely installed and in place.
Figure 8:
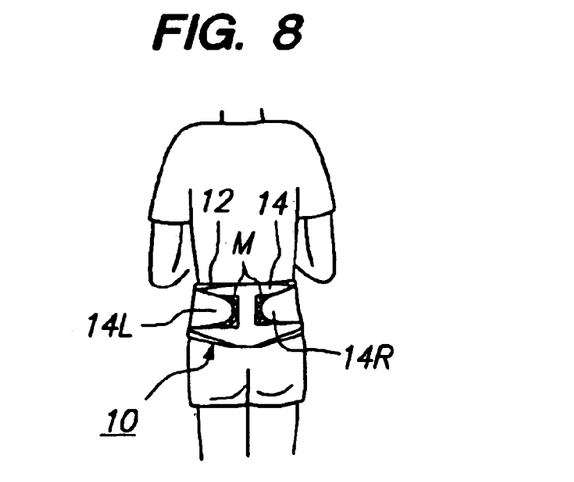
FIG. 8 is a rear view of FIG. 7.

Meanwhile, as shown in FIGS. 5 and 6, two left and right longitudinal ends (14L, 14R) of the back belt member (14) are respectively held by the hands and expanded to a front side similar to the two left and right longitudinal ends (12L, 12R) of the front belt member (12), while resisting the contractile force produced thereby, the two left and right pieces (14L, 14R) are inserted between the direction changing means (20) and the posterior surface of the front belt member (12). Upon insertion, the direction of the two left and right pieces (14L, 14R) of the back belt member (14) are directed to reverse directions (that is, directed posteriorly) by folding them around the direction changing means (20) by a half turn. Further, as shown by FIGS. 7 and 8, the two left and right longitudinal ends of the back belt member (14L, 14R) are further extended and attached at the means for attachment (M) at the posterior surface of the back belt member (14) and the means for attachment (M) provided at the left longitudinal end (14L) and the right longitudinal end (14R) of the back belt member (14) are brought into contact with each other and fixed to each other.

Further, in this case, the end portions of the two left and right folded-back pieces of the back belt member (14) can also be fixed to each other at the waist.

Clinical Data

EXAMPLE 1

Increase and Decrease of the Forward Bending Degree

A radiograph of a patient diagnosed with muscular lumbago was taken by the inventors. The plain X-ray photograph was taken fromthea side when the patient was wearing the corset (10) and when the patient was not wearing the corset (10), while the patient was sitting on a chair, stretching the arms at a height of the shoulder and lightly hanging on a handrail.

Figure 9:
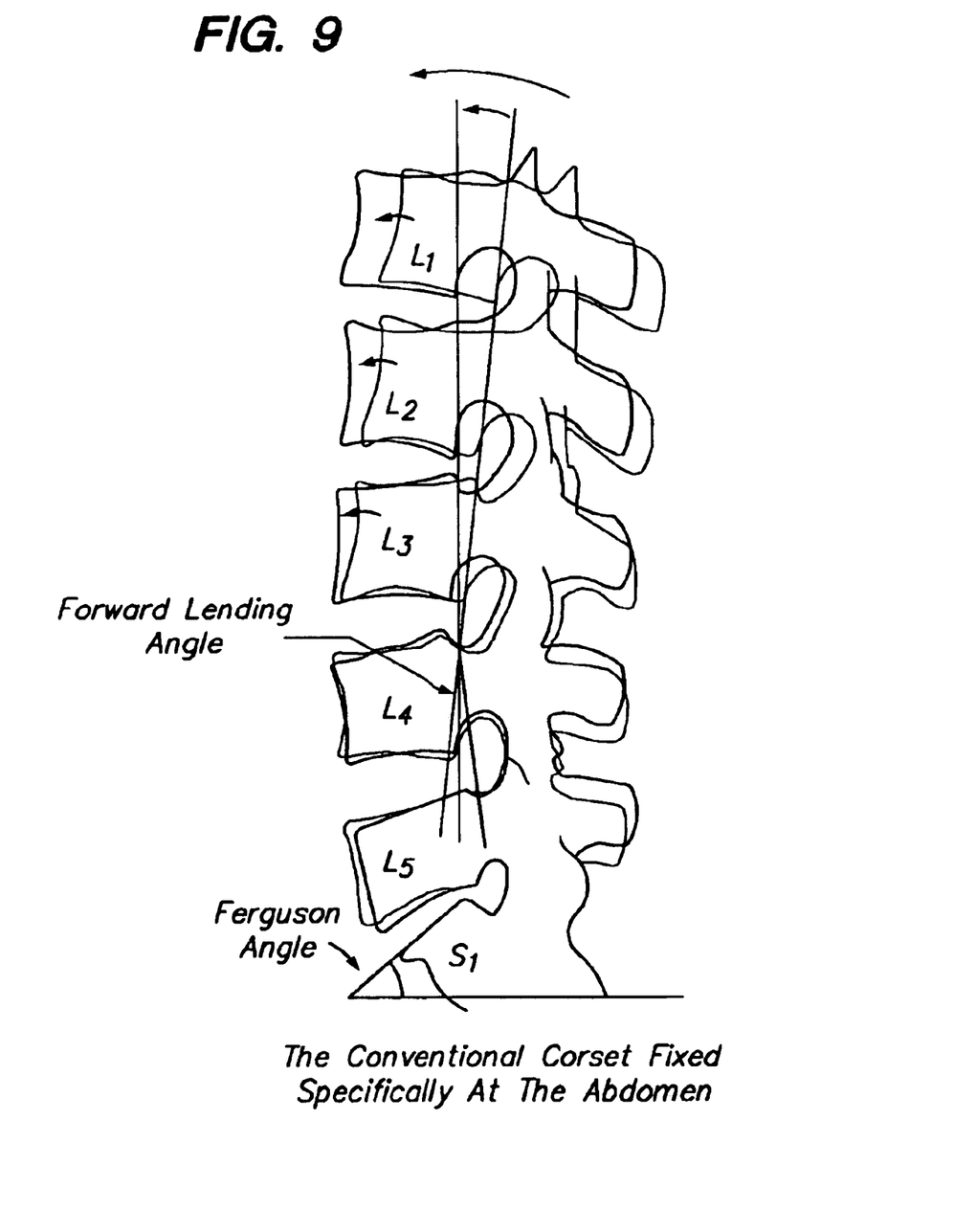
FIG. 9 is a schematic view of a radiograph of the spine while a conventional corset specifically fixed at abdomen is worn.
Figure 10:
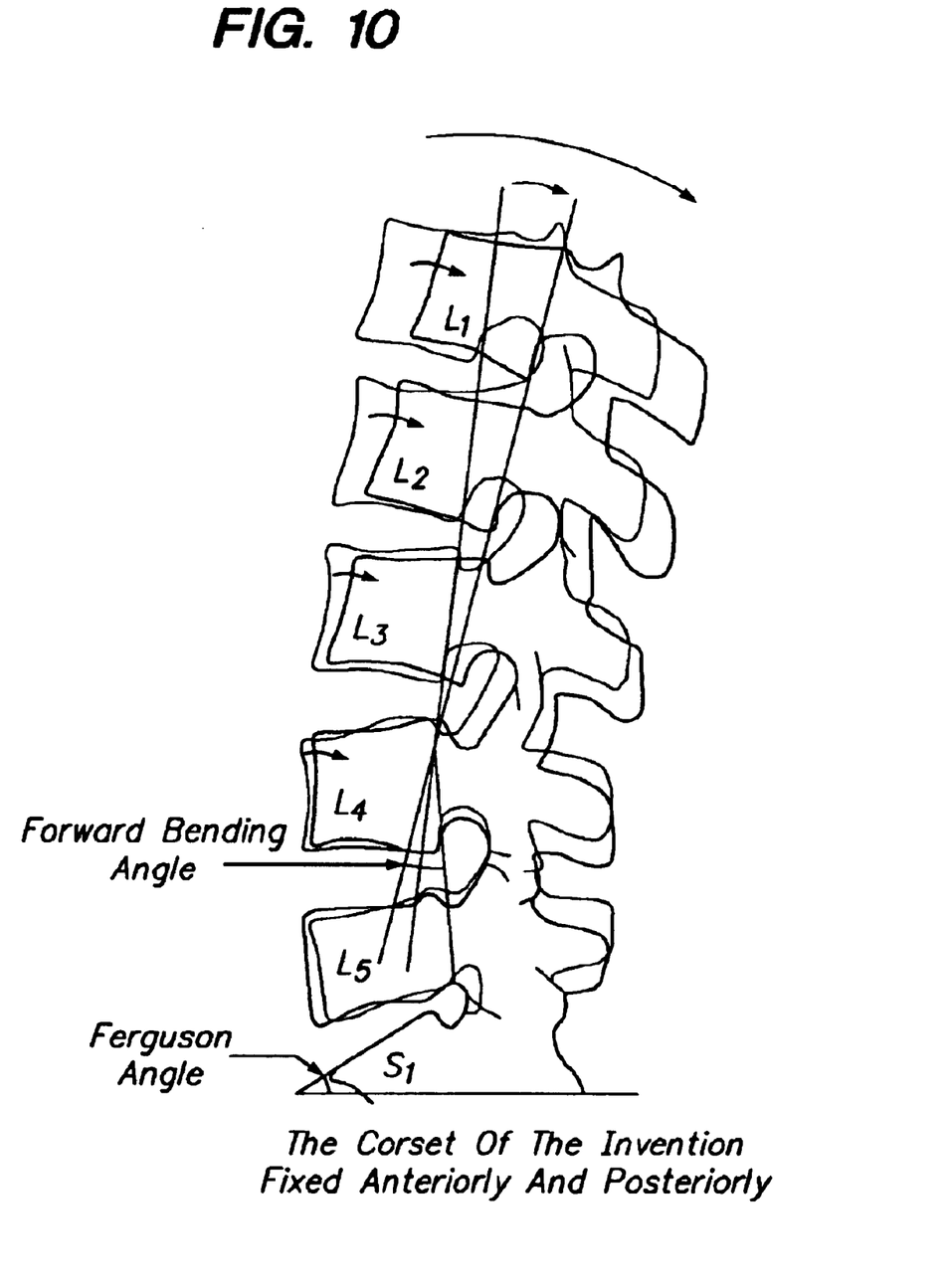
FIG. 10 is a schematic view of a radiograph of the spine while a corset according to the invention is worn.

From the radiographic image taken in this way, there is defined a forward bending degree by an angle made by a line parallel with the rear edge of the first lumbar and a line parallel with the rear edge of the fifth lumbar and a change between a case wearing the corset (10) and a case not wearing the corset (10), was compared between a group treated with the belt-like extensile corset of the invention and a group of the conventional type. FIGS. 9 and 10 show schematic views of X-ray photographs comparing the both groups.

As is apparent from the views, when a corset is fixed specifically at the abdomen (refer to FIG. 9), the spine is moved forwardly as a whole and the forward bending degree is decreased and when the corset (10) of the invention is worn (refer to FIG. 10), the backbone is conversely moved rearwardly and the forward bending degree is increased.

EXAMPLE 2

Twenty-three (23) patients were diagnosed with muscular lumbago by the inventors, orthopaedic surgeons. Among them, persons having an odd numbered birth date (12) are assigned to the extensile corset (10) group and persons having an even numbered birth date (11) were assigned to the conventional corset.

Figure 11:
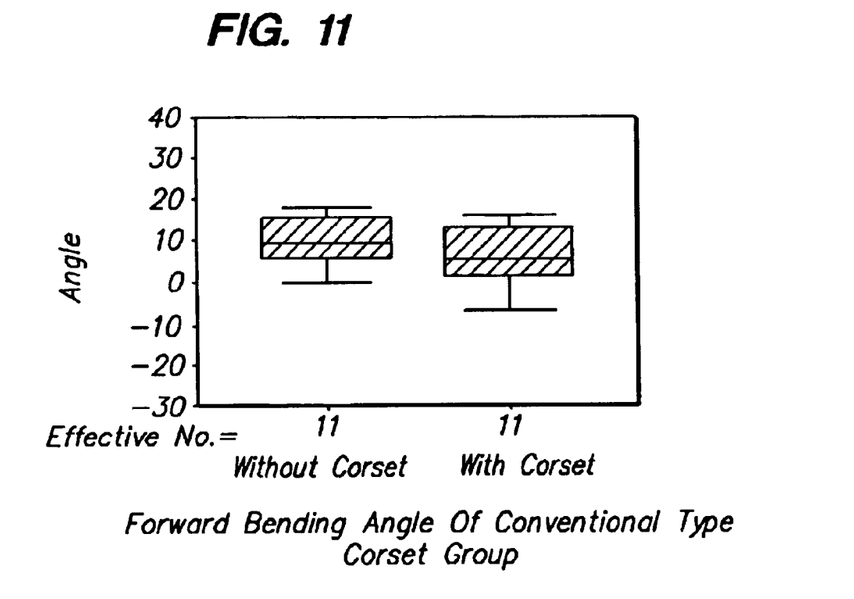
FIG. 11 is a graph of the change in the forward bending angle (forward bending degree) in eleven patients wearing conventional corsets.

A change in the forward bending degree was measured in the 23 patients. FIG. 11 compares a patient wearing the conventional corset and wearing nothing. Here, the forward bending degree in decreased and the spine was moved anteriorly.

Figure 12:
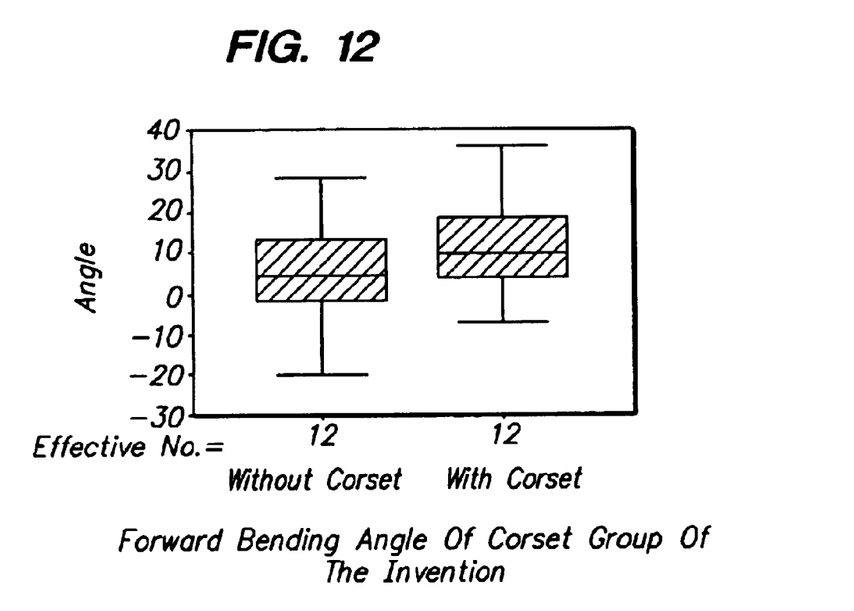
FIG. 12 is a graph of the change in the forward bending angle (forward bending degree) in twelve patients wearing the corset according to this invention.

FIG. 12 measures the change in the forward bending degree similarly using the extensile corset (10) of the invention. By wearing the corset (10) of the invention, the forward bending degree is increased and the spine was moved posteriorly. By moving the spine posteriorly, the stoop is rectified, the breast is spread and the posture is improved.

Numerically speaking, whereas in the group of the conventional type, the lumbar forward bending degree is 9.9±6.1 degrees before wearing the corset, after wearing the corset, the forward bending degree is decreased to 6.1±8.4 degrees, statistically significantly (p=0.026).

That is, in wearing the conventional type corset, the corset is fastened (fixed) on the anterior abdominal portion and therefore, the belly portion is pressed from the front side, the back muscle is relaxed and therefore, the forward bending degree of the lumbar is decreased (FIG. 9).

In the group wearing the extensile corset (10) of the invention, the lumbar forward bending degree is 6.2±13.4 degrees before wearing the corset and when wearing the corset (10), the forward bending degree it is increased to 11.3±12.3 degrees statistically significantly (p=0.008). That is, it is objectively confirmed that by wearing the corset (10) of the invention, the lumbar spine is provided with a contractile force opposite to that of the conventional type corset such that the back muscle is stretched, the abdomen extends anteriorly and the forward bending of the lumbar spine is increased (FIG. 10).

Quebec Pain Disability Index

In clinical evaluation, a comparison was made in patients between before treatment and after one week of treatment using the Quebec index (total marks of the degree of lumbago answered by the patients from 0 mark to 5 marks in 20 items of daily life motion, the most serious symptoms being is 100 marks).

That is, an evaluation made by marks of [Table 2] shown below with regard to 20 items of questions of [Table 1] shown below.

TABLE 1

| 01 | Rise from bed |
| 02 | Pain at night? |
| 03 | Turn over in bed |
| 04 | Stand for 20–30 minutes |
| 05 | Sit for one hour or more |
| 06 | Sit on low chair |
| 07 | Walk for about 15 minutes |
| 08 | Walk for about 1 hour |
| 09 | Walk with load on both hands |
| 10 | Walk on stairs |
| 11 | Run by about 100 m |
| 12 | Wear socks |
| 13 | Ride on vehicle |
| 14 | Take article on high shelf |
| 15 | Open heavy door |
| 16 | Throw ball lightly |
| 17 | Take article in refrigerator with slouch |
| 18 | Bring mat up and down |
| 19 | Clean bath by sponge |
| 20 | Bring up traveling bag to rack |

TABLE 2

| No pain at all | 0 mark |
| Slightly difficult | 1 marks |
| Sometimes difficult | 2 marks |
| Frequently difficult | 3 marks |
| Always difficult | 4 marks |
| Cannot at all | 5 marks |

All of the patients were administered with the same nonsteroidal species analgesic and wet compress pad as a combined treatment. With regards to the time period for wearing the corset, all of the patients were guided to wear the corsets as long as possible other than whiel asleep. The Wilcoxon test was used for statistical testing.

Figure 13:
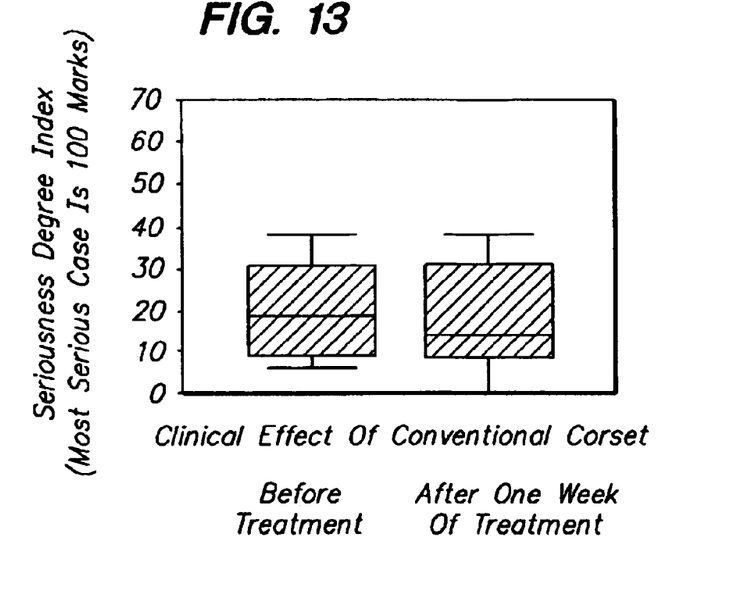
FIG. 13 is a graph diagram showing a change in a Quebec pain disability index after one week of wearing the conventional corset.
Figure 14:
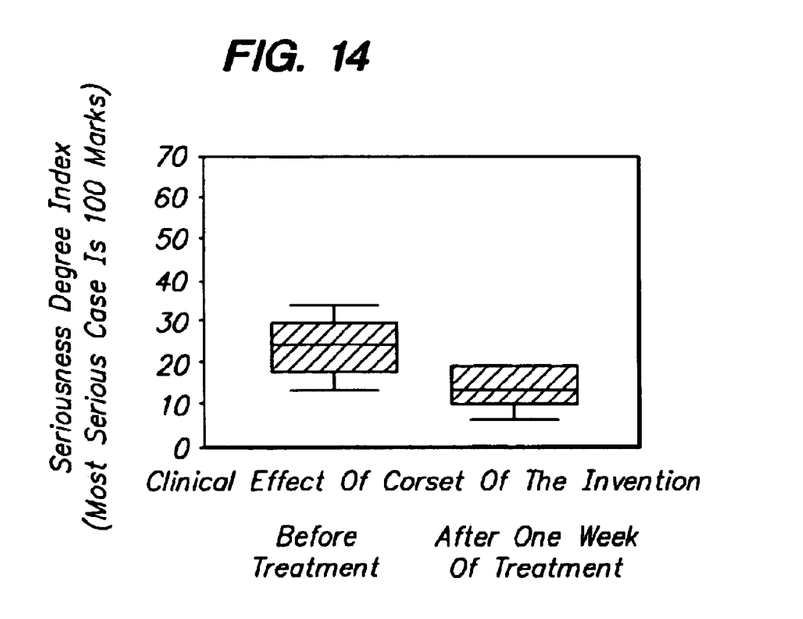
FIG. 14 is a graph diagram showing a change in the Quebec pain disability index after one week of wearing a corset according to the invention.

As is shown by combaring FIGS. 13 and 14, there was a statisitically significant difference in the effect of wearing the corset (10) of the invention and wearing the conventional corset.

In this way, at the time point of one week after treatment began, the treatment result was better with the corset (10) of the invention than with the conventional type corset and the corset (10) of the invention provided prompt healing.

EXAMPLE 3

The inventor studied the use of the belt-like extensile corset in centrally obese and non-centrally obese participants and reported significant improvement concordant with maintenance of the lumbar lordosis, suggesting that lordotic seated posture is more likely to alleviate low back pain in this population. Waist-hip ratio was used to evaluate central obesity. Males with a waist-hip ratio over 90% and females with a ratio over 80% were considered obese. An advantage of using this measurement is that, whereas body mass index ranges differ among racial groups (e.g. Japanese and Caucasian), definitions of central obesity by waist-hip ratio remains consistent. Kameda T, Ito M, Chun W, et al, 9 OFFICIAL JOURNAL OF THE JAPANESE SOCIETY OF HUMAN DRY DOCK 31–6 (1994) (in Japanese), Perry A C, Miller P C, Allison M D, et al, 68 AM J CLIN NUTR 1022–7 (1998).

Lumbosacral corsets with tension from front to back according to this invention were assembled to evaluate for symptomatic and anatomic geometric changes, as well as assess for differences in response rate, controlling for a central obesity pattern.

One hundred and forty three (143) new outpatients with chronic low back pain for longer than 3 months, with neither a positive straight leg raise test nor radiographic abnormality including lumbar spondylosis, were treated with the traditional lumbosacral corset or one with a front to back tensile band (extensile corset) for four weeks. Patients were divided according the presence of central obesity. Randomization was performed according to birthday.

Outcome was measured using the Quebec Back Pain Disability Scale, Kopec J A, 20 SPINE 341–52 (1995), and bony alignment was assessed by radiographs to analyze the change in sacral inclination angle with and without the respective corset. Quebec Back Pain Disability Scale scores were measured at baseline and at 4 weeks.

The angle of sacral inclination was determined by measuring the angle between the superior line of the sacrum and the horizontal on radiographs according to the method of Korovessis P, Stamatakis M & Baikousis 12 J SPINAL DISORD 131–7 (1999). This is also measured with Ferguson's angle.

Analysis for correlation between sacral inclination angle without corsets and W/H ratio was performed. The sacral inclination angle was radiographically compared with and without corset use. The radiographic assessment was determined by three orthopedic surgeons prior to being informed of the category of the patients. The Quebec Back Pain Disability Scale at the final assessment was compared with baseline in each group. The percentage of remission was calculated by dividing the difference between final assessment and baseline scores by the baseline score and multiplying by 100%.

The mean changes in sacral inclination were +3.8±5.4 degrees in the extensile corset group (n=72) and −2.6±4.6 degrees in the traditional corset group (n=71). Thus, the extensile corset had a mechanical effect opposite to the traditional corset. Participants without central obesity, treated with the extensile corset (n=30), demonstrated significant improvement compared with participants with the traditional corset (n=33), (p=0.034). The subgroup of participants without central obesity in the extensile corset group demonstrated significantly greater improvement than participants treated with traditional corsets (p=0.034). In the extensile corset group, the percentage of remission was improved significantly in the non-central obesity subgroup compared with the central obesity subgroup (p=0.011).

From the foregoing description, various modifications and changes in the compositions and methods of this invention will occur to those skilled in the art. All such modifications coming within the scope of the appended claims are intended to be included therein. Those skilled in the art will find it apparent that various modifications and variations can be made to the formulations of this invention. Thus, the present invention is intended to cover such modifications and variations, provided that they come within the scope of the appended claims and their equivalents.

The disclosures of all publications cited above are expressly incorporated by reference in their entireties to the same extent as if each were incorporated by reference individually.

FIG. 1
POSTERIOR VIEW OF PREFERRED EMBODIMENT
FIG. 2
PERSPECTIVE VIEW OF PREFERRED EMBODIMENT
FIG. 3
FORWARD FASTENING
FIG. 4
FORWARD FASTENING
FIG. 5
BACKWARD FASTENING
FIG. 6
BACKWARD FASTENING
FIG. 9
FORWARD BENDING ANGLE
FERGUSON ANGLE
THE CONVENTIONAL CORSET FIXED SPECIFICALLY AT THE ABDOMEN
FIG. 10
FORWARD BENDING ANGLE
FERGUSON ANGLE
THE CORSET OF THE INVENTION FIXED ANTERIORLY AND POSTERIORLY
FIG. 11
ANGLE
EFFECTIVE NO
WITHOUT CORSET
WITH CORSET
FORWARD BENDING ANGLE OF CONVENTIONAL TYPE CORSET GROUP
FIG. 12
ANGLE
EFFECTIVE NUMBER
WITHOUT CORSET
WITH CORSET
FORWARD BENDING ANGLE OF CORSET GROUP OF THE INVENTION
FIG. 13
QUEBEC PAIN DISABILITY INDEX [MOST SERIOUS CASE IS 100 MARKS]
BEFORE TREATMENT
CLINICAL EFFECT OF CONVENTIONAL TYPE CORSET
AFTER ONE WEEK OF TREATMENT
FIG. 14
QUEBEC PAIN DISABILITY INDEX [MOST SERIOUS CASE IS 100 MARKS]
BEFORE TREATMENT
AFTER ONE WEEK OF TREATMENT
CLINICAL EFFECT OF CORSET OF THE INVENTION

I claim:
1. A belt-like corset comprising:
a) two longitudinally expandable front and back belt members each having an inner and outer surface, opposite lateral edge portions, longitudinal centers, longitudinal ends, and right and left side portions adapted to be positioned at the lateral left and right side of a wearer;
b) said back belt member is fixedly attached to said front belt member at about their longitudinal centers;
said fixedly attached longitudinal centers adapted to be positioned at the center of a back of a wearer;
c) means for attaching the longitudinal ends of the front belt member to each other;
d) two direction changing means for said back belt member located on the outer surface of the front belt member positioned so as to be present on the left and right side of a wearer, wherein each of said direction changing means is a ring like article having two end portions that are attached to said opposite lateral edge portions of the front belt member so as to extend vertically;
e) means for attaching the longitudinal ends of the back belt member to the outer surface of the back belt member lateral and substantially adjacent to said fixedly attached longitudinal centers.

2. A method for treating lower back pain in a human comprising the use of a belt-like corset comprising the steps of:
a) providing a one-piece extensile corset comprising two longitudinally expandable front and back belt members each having an inner and outer surface, longitudinal centers, longitudinal ends; opposite lateral edge portions, and right and left side portions, adapted to be positioned at the lateral left and right side of a wearer;
b) providing fixedly attached means to attach said belt members to each other at about their longitudinal centers;
c) providing means to attach the longitudinal ends of the front belt member to each other;
d) providing two direction changing means for said back belt member located on the outer surface of and on the right and left side portion of said front belt member positioned so as to be present on the left and right side of a human when worn;
e) providing means to attach the longitudinal ends of the back belt member to the outer surface of the back belt member located lateral to and substantially adjacent to said fixedly attached longitudinal centers;
f) placing the front and back belt members behind the waist of said human such that their attached portion is behind the spinal column of said human;
g) wrapping the front belt member around the human body against a contraction force produced by its elasticity;
h) attaching the longitudinal ends of said front belt member to each other by attachable and detachable means of a face fastener at the ventral portion of the waist of said human;

i) expanding the longitudinal ends of said back belt member to a front side, inserting said back belt members under said direction changing means, folding back to a rear side against a contraction force produced by their elasticity;

j) attaching the longitudinal ends of said back belt member to the outside surface of said back belt member at a position lateral and substantially adjacent to the attached longitudinal centers.

3. The method of claim 2 wherein said low back pain is caused by disc degeneration, disc herniation, or lumbago.

4. The method of claim 2 wherein said human is of normal weight.

5. The method of claim 2 wherein said human is male and has a waist to hip ratio of 90 degrees or less.

6. The method of claim 2 wherein said human is female and has a waist to hip ratio of 80 degrees or less.

* * * * *

UNITED STATES PATENT AND TRADEMARK OFFICE
CERTIFICATE OF CORRECTION

PATENT NO. : 6,755,799 B2
DATED : June 29, 2004
INVENTOR(S) : Toda

It is certified that error appears in the above-identified patent and that said Letters Patent is hereby corrected as shown below:

<u>Column 1,</u>
Line 6, should read -- The patent application claimed priority based on Japanese application number 2001-253516 filed August 23, 2001.

Signed and Sealed this

Tenth Day of August, 2004

JON W. DUDAS
*Acting Director of the United States Patent and Trademark Office*